(12) United States Patent
Gu et al.

(10) Patent No.: US 11,116,479 B2
(45) Date of Patent: Sep. 14, 2021

(54) TIME-BASED PARAMETRIC CONTRAST ENHANCED ULTRASOUND IMAGING SYSTEM AND METHOD

(71) Applicant: KONINKLIJKE PHILIPS N.V., Eindhoven (NL)

(72) Inventors: Xiaolin Gu, Shanghai (CN); Yinhui Deng, Shanghai (CN); Xiaomin Li, Shanghai (CN); Vijay Thakur Shamdasani, Kenmore, WA (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 622 days.

(21) Appl. No.: 15/859,792

(22) Filed: Jan. 2, 2018

(65) Prior Publication Data
US 2018/0185010 A1   Jul. 5, 2018

(30) Foreign Application Priority Data

Jan. 4, 2017 (WO) ................ PCT/CN2017/070119

(51) Int. Cl.
| | |
|---|---|
| *A61B 8/08* | (2006.01) |
| *A61B 8/14* | (2006.01) |
| *A61B 8/06* | (2006.01) |
| *G06T 11/00* | (2006.01) |
| *G06T 11/20* | (2006.01) |
| *G06T 11/60* | (2006.01) |

(52) U.S. Cl.
CPC .............. *A61B 8/5207* (2013.01); *A61B 8/06* (2013.01); *A61B 8/08* (2013.01); *A61B 8/085* (2013.01); *A61B 8/14* (2013.01); *A61B 8/481* (2013.01); *G06T 11/001* (2013.01); *G06T 11/206* (2013.01); *G06T 11/60* (2013.01); *G06T 2210/41* (2013.01)

(58) Field of Classification Search
CPC ......... A61B 8/5207; A61B 8/06; A61B 8/085; A61B 8/481; A61B 8/14; A61B 8/08; G06T 2210/41; G06T 11/001; G06T 11/206; G06T 11/60
See application file for complete search history.

(56) References Cited

U.S. PATENT DOCUMENTS

| | | | |
|---|---|---|---|
| 5,706,819 | A | 1/1998 | Hwang et al. |
| 5,833,613 | A | 11/1998 | Averkiou et al. |
| 6,186,950 | B1 | 2/2001 | Averkiou et al. |
| 6,692,438 | B2 | 2/2004 | Skyba et al. |

(Continued)

FOREIGN PATENT DOCUMENTS

| | | |
|---|---|---|
| EP | 2417912 A1 | 2/2012 |
| WO | 2015104607 A1 | 7/2015 |

*Primary Examiner* — Bill Thomson
*Assistant Examiner* — Amal Aly Farag (57) ABSTRACT

An ultrasonic diagnostic imaging system and method acquire a sequence of image data as a bolus of contrast agent washes into and out of the liver. The image data of contrast intensity is used to compute time-intensity curves of contrast flow for points in an ultrasound image. Time-dependent data is calculated from the data of the time-intensity curves which, in a described implementation, comprise first and second derivatives of the time-intensity curves. A color map is formed of the time-dependent data or the polarities of the data and displayed in a parametric image as a color overlay of a contrast image of the liver.

15 Claims, 5 Drawing Sheets

(56) References Cited

U.S. PATENT DOCUMENTS

| | | |
|---|---|---|
| 8,971,600 B2 | 3/2015 | Yoshikawa et al. |
| 2004/0120559 A1 | 6/2004 | Hall |
| 2009/0028406 A1* | 1/2009 | Arditi ...................... A61B 8/06 |
| | | 382/131 |
| 2011/0208061 A1 | 8/2011 | Chang |
| 2012/0027282 A1* | 2/2012 | Yoshikawa .............. A61B 8/13 |
| | | 382/131 |
| 2015/0257739 A1 | 9/2015 | Yao et al. |
| 2015/0371379 A1* | 12/2015 | Averikou ............ A61B 8/5284 |
| | | 382/128 |
| 2016/0253800 A1* | 9/2016 | Gurevich ............... A61B 5/445 |
| | | 382/128 |

* cited by examiner

TIME-BASED PARAMETRIC CONTRAST ENHANCED ULTRASOUND IMAGING SYSTEM AND METHOD

FIELD OF THE INVENTION

This invention relates to medical ultrasound imaging systems and, in particular, to parametric contrast enhanced imaging of time-based parameters.

BACKGROUND OF THE INVENTION

Hepatitis B and hepatitis C patients have been found to be at an increased risk of developing primary liver cancer, hepatocellular carcinoma (HCC). Due to the discovery that hepatitis C was being contracted by patients through blood transfusions in the early 1980's, there remain a significant number of hepatitis C patients who need to be examined regularly for the onset of HCC, as the lesions are best treated in their early stages. The usual progression of the disease is from hepatitis to liver cirrhosis to HCC. An easy-to-use monitoring technique for liver disease progression would have widespread application in assisting in the early detection of this serious disease.

Since liver lesions, like other cancers, are most effectively treated when detected early, high-risk patients should be monitored frequently for signs of these diseases. But in their early stages liver lesions are often difficult to detect through conventional diagnostic imaging due to their small size. Thus, clinicians often conduct their diagnoses to look for other signs that a lesion is developing. One of these signs is changes in the blood flow to the liver. The liver has a unique blood supply network. A primary source of fresh blood to the liver is the arterial inflow from the hepatic artery. But the liver has a secondary blood supply, the portal vein in the abdomen. Being both arterial and venous, these sources of supply function differently. The pulsatile flow of blood from the hepatic artery occurs shortly after systole, like other arterial vessels. The inflow of blood from the portal vein occurs later in the heart cycle. It has been found that the vascular network which develops to supply blood to a lesion is generally arterial, whereas the blood supplied to normal parenchyma is generally venous. Thus, the relative timing and amount of blood flow from these two sources, if such can be separately distinguished, can lead to effective lesion diagnosis. One technique which can distinguish these different flows of blood is ultrasonic contrast imaging with microbubble contrast agents. In a typical procedure, the subject is infused with either a bolus injection of the contrast agent, or with continuous infusion of the agent. Following a bolus injection a tumor in the liver will "light up" as it is infused with the arrival of contrast agent from the hepatic arterial blood supply. Normal tissue in the liver lights up at a later time when the bolus of contrast agent enters the liver through the portal vein. At this later time the tumor will appear similar to or less bright than the surrounding normal tissue. The same effect can be obtained by flash destruction of the microbubbles in a continuous infusion, followed by observation of the reperfusion of the contrast agent in the liver from the arterial and venous sources.

But these temporal changes in the ultrasound liver can be subtle and difficult to discern clearly. In part, this is because the wash-in and wash-out of contrast agent from the two blood supplies overlap in time. To better discern the different effects, parametric imaging has been employed in which the anatomical image is colored in accordance with one or more parameters of time-intensity curves of wash-in and wash-out at points in the liver image where perfusion occurs. As the contrast agent builds up in the tissue during wash-in and decreases during wash-out, the intensity of the agent throughout the image field is continually detected and recorded. A curve is formed of the recorded contrast intensity data using any of a number of known curve-fitting equations or smoothing techniques. Parameters of the resulting curve equation, such as peak intensity of the curve, time to peak intensity, mean slope of the rise of the curve, full wash-in, wash-out time, etc. are then color-coded and displayed in an overlay of the anatomical image. Temporal parametric images can reveal differences in perfusion at the different phases of this diagnostic process.

SUMMARY OF THE INVENTION

While parametric contrast imaging has been found to aid in liver tumor diagnosis, it is limited because a contrast image is static, representing parameters of the full curve or occurring at a selected time in the reperfusion process. Such static parameters can make it difficult to separate two processes which overlap in time such as the arterial and venous flows in the liver. Thus, it is desirable to be able to produce parametric images of the characteristics of blood flow in the liver which are better able to distinguish between flow from these two sources, so that tumorous tissue can be more effectively distinguished from normal tissue.

In accordance with the principles of the present invention a system and method are described for distinguishing between tumorous and healthy tissue in parametric contrast enhanced liver imaging. Ultrasonic contrast image data is acquired as contrast agent washes in and out of the liver, and time-intensity curves are produced for points in the image field where perfusion occurs. Time-dependent parameters of the change in intensity are computed for each curve. In a preferred implementation this computation is performed by calculating first and second derivatives at points along the time-intensity curves. A parametric image is then produced using the time-dependent parameters. In an implementation described below, blood flow from the different sources to the liver is more sharply distinguished by a parametric image of the polarity of the time-based parameters rather than an image of ranges of parameter magnitudes. These parametric images can be formed following acquisition of contrast echo data for a complete wash-in, wash-out cycle, or in real time as the echo data is acquired.

DETAILED DESCRIPTION

Figure 1:
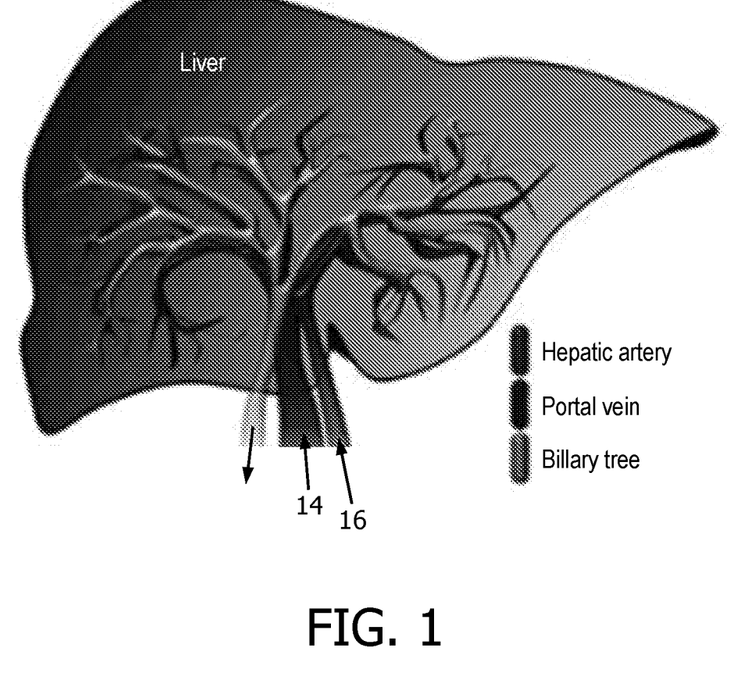
FIG. 1 is an illustration of the liver, showing the entry of the hepatic artery and portal vein blood flows into the bottom of the organ.

FIG. 1 is an illustration of the liver and its flow network. The liver contains vessel trees for three sources of flow: the biliary tree for the flow of liver bile, the portal vein 14 which provides a nourishing flow of blood from the abdomen, and the hepatic artery 16 which is a source of arterial blood flow. The capillary structures of these networks are intertwined throughout the parenchyma, causing liver tissue to be perfused with blood from both arterial and venous sources. The hepatic artery 16 and portal vein 14 can be accessed separately where they enter the organ at the bottom of the liver as shown in the illustration. As mentioned above, a liver lesion gets most of its flow of nourishing blood from the hepatic artery, whereas normal tissue receives its primary blood flow from the portal vein. It is an object of the present invention to distinguish whether a location in the parenchyma is receiving blood flow primarily from the hepatic artery or the portal vein.

Figure 2:
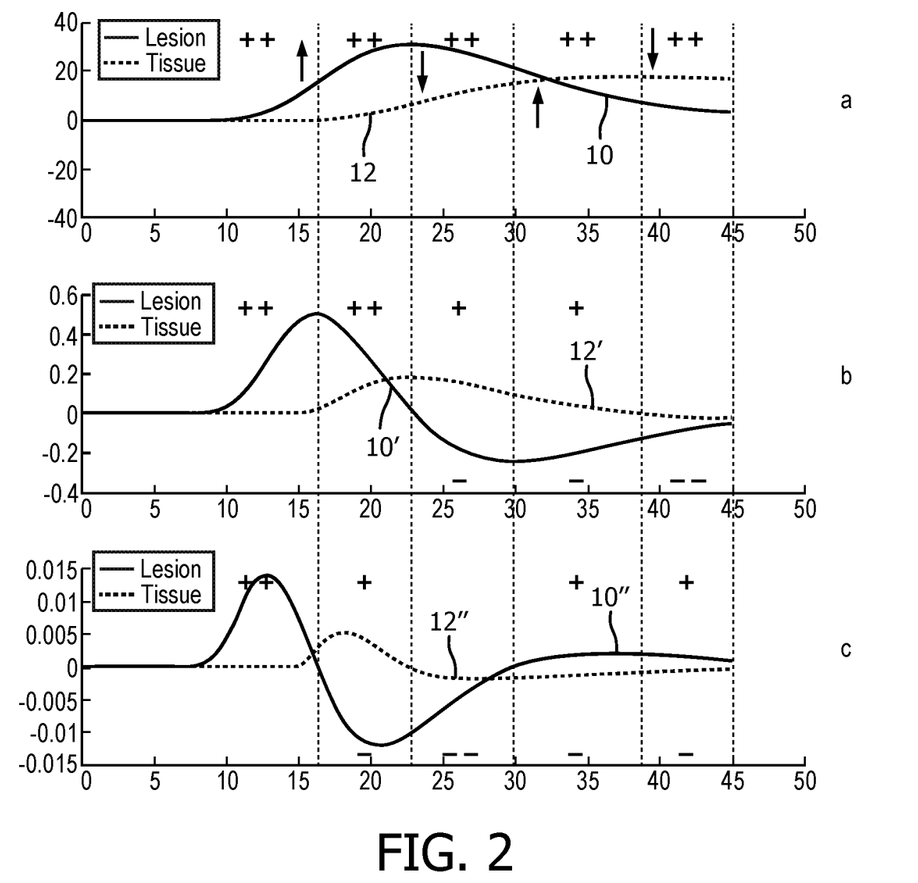
FIG. 2 illustrates time-intensity curves of lesions and normal tissue, and time-based parametric curves produced therefrom.

FIG. 2 shows time-intensity curves produced from contrast intensity echo data which illustrates how this objective is achieved in accordance with the present invention. This drawing illustrates three time-aligned plots of time-intensity curves produced during a wash-in, wash-out cycle. The horizontal time axis extends to fifty second and is shown divided into successive time periods by dashed vertical lines. The vertical axis is a magnitude scale. The two curves in the top area a. are a time-intensity curve 10 produced using contrast echo data from a lesion, and a time-intensity curve 12 produced using contrast echo data from normal tissue. The time-intensity curve 10 of contrast flow to a lesion starts to rise at the ten second mark, as indicated by the upward-pointing arrow above the curve. At the twenty-three second mark the flow of contrast agent at the lesion peaks and thereafter declines during wash-out as indicated by the downward-pointing arrow below the curve. The time-intensity curve 12 of contrast flow in normal tissue from the portal vein begins to arrive at the seventeen second mark and rises during wash-in as indicated by the upward-pointing arrow below the curve. The contrast flow peaks around the thirty-eight second point and thereafter declines during wash-out as indicated by the downward-pointing arrow above the curve. It is seen that there is considerable overlap of these curves, with the contrast flow in the lesion already on the decline as the contrast agent is just beginning to arrive in the normal tissue.

Figure 3:
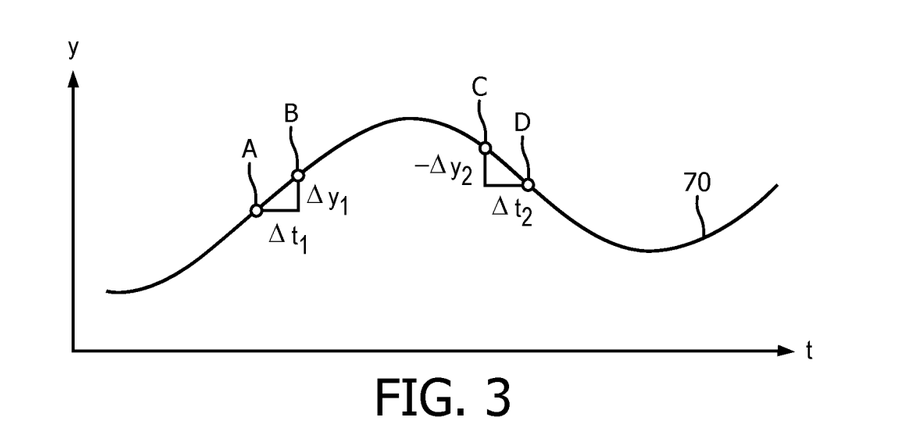
FIG. 3 illustrates the computation of positive and negative time-based parameters of a curve.

In accordance with the principles of the present invention, parametric curves 10' and 12' are shown in area b. of FIG. 2. The curve 10' is a plot of the continuous rate of change of curve 10, which is produced by computing the first derivative, a time-dependent derivative dI/dt, of time-intensity curve 10. This calculation is illustrated in FIG. 3, which shows a curve 70 which varies in both intensity (amplitude) and with time. A first derivative of the changing amplitude is calculated by taking two points on the curve such as point A and point B, each of which has a unique amplitude y and a time value t. The changing amplitude using these two points is calculated as $$\frac{\Delta y}{\Delta t}$$

where $\Delta y$ difference in amplitude (contrast intensity I) from point A to point B, and $\Delta t$ is the difference in time between the two points. The first derivative of time-intensity curve 10 of FIG. 2a is calculated using successive points along the curve to calculate successive points of curve 10' in FIG. 2b. The same process is used with the points of curve 12 to compute curve 12', the rate of change of the intensity of curve 12. It is seen that the curves 10' and 12' are much more different from each other than are the original intensity curves 10 and 12. Thus, a parametric image of the first derivatives of time-intensity curves throughout the image area will more sharply distinguish between normal tissue and lesions than will a parametric image of a parameter of the original time-intensity curves.

Area c. of FIG. 2 shows curves derived by repeating the derivative calculations a second time, which are curves 10" and 12" formed by computing the second derivatives of the original time-intensity curves 10 and 12. This calculation is also illustrated by FIG. 3 where, in this instance, curve 70 represents one of the first derivative curves of FIG. 2b. The difference in amplitude of successive points along the first derivative curve, $\Delta y$, is calculated for the time interval between the successive point, $\Delta t$, to form $$\frac{\Delta y}{\Delta t}$$

the first derivative curve, which is the second derivative of the original time-intensity curve. The curves 10" and 12" of FIG. 2c are the acceleration of the change in intensity of the original time-intensity curves 10 and 12. It is seen that curves 10" and 12" are even more sharply different than the first derivative curves 10' and 12', and a functional image using the second derivative of the time-intensity curves at each point in a parametric image will more greatly distinguish normal tissue from lesions in the parametric image.

FIG. 2 illustrates how even more sharply distinguishing parametric images can be formed from the derivative computations, which is to form a binary parametric image of just the curve polarity. In FIG. 2a it is seen that the two time-intensity curves are always positive with respect to the zero amplitude level. This is indicated for each of the five time intervals of the drawing by the polarity "+" signs in each interval of zero to sixteen seconds; sixteen to twenty-three seconds; twenty-three to thirty seconds; thirty to thirty-nine seconds; and thirty-nine to forty-five seconds. The two "+" signs in each time interval indicate that each time-intensity curve is positive during the respective time interval.

FIG. 2b yields a different result. The first derivative curve 10' has a positive sign throughout the first two intervals until the twenty-three second mark at the end of the second interval. Thereafter, the curve 10' has a negative sign, a declining rate of change, as indicated by the "−" signs below curve 10' in the last three time intervals. Thus, a parametric image of the polarity taken for any point in time after twenty-three seconds of the wash-in, wash-out cycle will show different values for tumors and normal tissue. This is illustrated in FIG. 3, where a first derivative using points C and D is computed as $$\frac{-\Delta y_2}{\Delta t_2},$$

which compares with the first derivative using points A and B of $$\frac{+\Delta y_1}{\Delta t_1}.$$

A similar result occurs with the second derivative curves of FIG. 2c. The curves 10" and 12" are both positive in the first interval before the sixteen second mark, and are both negative, a negative acceleration of the original time-intensity curves, in the third time interval from twenty-three to thirty seconds. In each other time interval the curves exhibit different polarities. Thus, a binary parametric image formed using just the signs of the first or second derivative calculations will greatly distinguish normal tissue from tumors in the parametric image. The differences may be highlighted by using distinguishing colors for the different polarities. Points in the image with one polarity can be colored green in the parametric image while points of the other polarity can be colored red, for instance. By examining such binary parametric images of derivative polarity computed at different points in the wash-in, wash-out cycle, regions of suspected tumors can be quickly spotted and diagnosed further.

Figure 4:
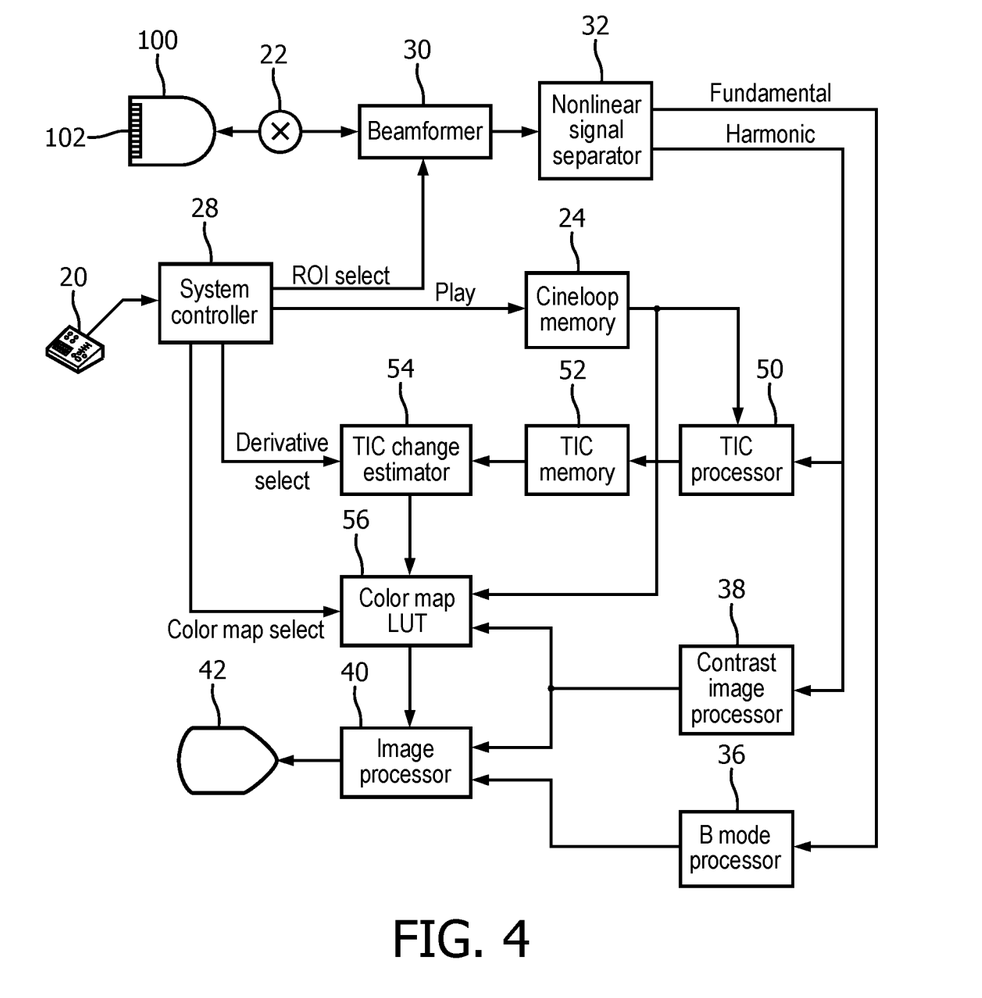
FIG. 4 illustrates in block diagram form an ultrasonic diagnostic imaging system constructed in accordance with the principles of the present invention.

Referring now to FIG. 4, an ultrasound system constructed in accordance with the principles of the present invention is shown in block diagram form. An ultrasonic probe 100 includes an array 102 of ultrasonic transducer elements that transmit and receive ultrasonic pulses. The array may be a one dimensional linear or curved array for two dimensional imaging, or may be a two dimensional matrix of transducer elements for electronic beam steering and focusing in two or three dimensions. The ultrasonic transducer elements in the array 102 transmit beams of ultrasonic energy by their timed actuation by a beamformer 30, and receive echoes returned in response to this transmission. A transmit/receive ("T/R") switch 22 is coupled to the ultrasonic transducers in the array 102 to selectively couple signals from the transducer elements to A/D converters in the beamformer 30 during the receive phase of operation. The times at which the transducer array is actuated to transmit signals may be synchronized to an internal system clock (not shown), or may be synchronized to a bodily function such as the heart cycle, for which a heart cycle waveform is conventionally provided by an ECG waveform sensor coupled to the ultrasound system. When the heartbeat is at the desired phase of its cycle as determined by the waveform provided by ECG sensor, the probe is commanded by a system controller to acquire an ultrasonic image.

Echoes from the transmitted ultrasonic energy are received by the transducer elements of the array 102, which generate echo signals that are coupled through the T/R switch 22 and digitized by the analog to digital converters when the system uses a digital beamformer. Analog beamformers may alternatively be used. The A/D converters sample the received echo signals at a sampling frequency controlled by a signal $f_s$ generated by a system controller 28. The desired sampling rate dictated by sampling theory is at least twice the highest frequency of the received passband, and might be on the order of 30-40 MHz. Sampling rates higher than the minimum requirement are also desirable. Control of the ultrasound system and of various control setting for imaging such as probe selection and ROI (region of interest) delineation is effected by user manipulation of the controls of a user control panel 20, such as keys, pushbuttons, a trackball or computer mouse, which is coupled to and applies its control through the system controller 28.

The echo signal samples from the individual transducers of the array 14 are delayed and summed by the beamformer 30 to form coherent echo signals along scanline directions for an image. The digital coherent echo signals may then be filtered by a digital filter and undergo noise reduction as by spatial or frequency compounding. The digital filter can also shift the frequency band to a lower or baseband frequency range. The digital filter could be a filter of the type disclosed in U.S. Pat. No. 5,833,613 (Averkiou et al.), for example. When phase information is needed as is the case for Doppler processing, quadrature (I and Q) demodulation may also be performed on the echo signals. In this implementation, the transmit frequency $f_o$ and the receiver frequency are individually controlled so that the beamformer 30 is free to receive a band of frequencies which is different from that of the transmitted band such as a harmonic frequency band around frequency $2f_o$.

The beamformed coherent echo signals are coupled to a nonlinear signal separator 32. The nonlinear signal separator 32 can separate second harmonic echo signals with a high pass filter, but preferably it separates harmonic frequency echoes returned from harmonic contrast agents by the pulse inversion technique, in which echo signals resulting from the transmission of multiple, differently phased (inverted) pulses to an image location are additively combined to cancel fundamental signal components and enhance harmonic components, thus producing echo signals in a harmonic band $2f_o$. The same echo signals are subtractively combined to produce echo signals in a fundamental frequency band $f_o$. A preferred pulse inversion technique is described in U.S. Pat. No. 6,186,950 (Averkiou et al.) and in U.S. Pat. No. 5,706,819 (Hwang et al.) for instance.

Figure 7:
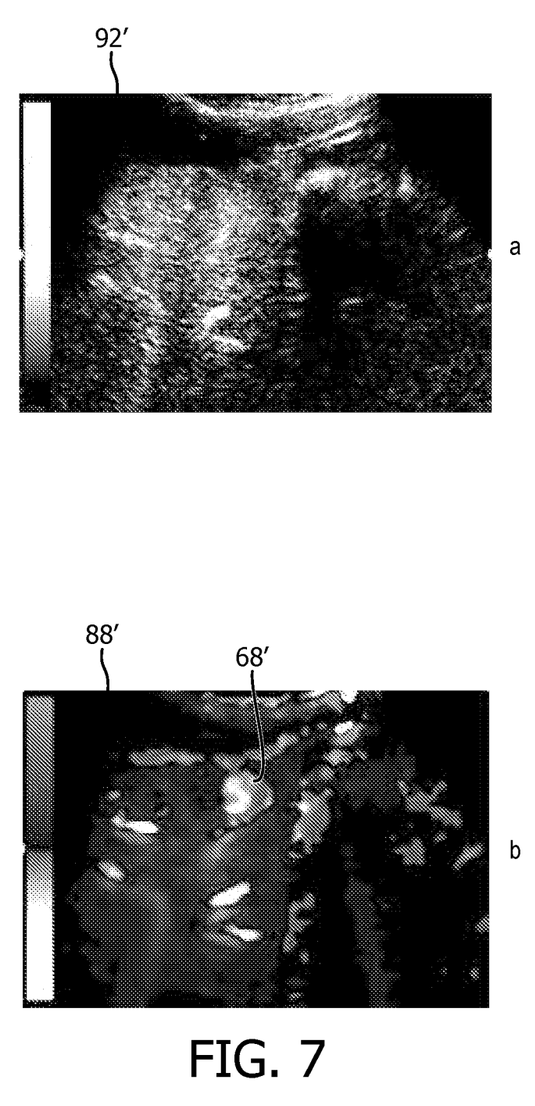
FIG. 7 illustrates contrast intensity image and a parametric contrast image produced in accordance with the method of FIG. 6.

Harmonic echo signals from a contrast agent, such as microbubbles, are coupled to a contrast image processor 38. Contrast agents are often used to more clearly delineate blood vessels, or to perform perfusion studies of the microvasculature of tissue as described in U.S. Pat. No. 6,692,438 (Skyba et al.) for example, which is hereby incorporated by reference. In the implementation shown in FIG. 4, echoes from a contrast agent are used to produce both a contrast image as shown in FIG. 7, and time-intensity curves from selected ROIs (individual pixel locations or groups of pixels) in the image field. For parametric images as described herein, a 3 by 3 group of pixels is preferred for an ROI size from which to form a time-intensity curve. The contrast image processor produces an anatomical contrast image by amplitude (or envelope) detection of the harmonic frequency echoes from each point in the image field. One way to do this when the echoes are quadrature demodulated is to calculate the signal amplitude at each pixel location in the form of $(I^2+Q^2)^{1/2}$. These contrast intensity signals are mapped to the desired display format by scan conversion which converts samples from R-θ coordinates to Cartesian (x,y) coordinates for display of a spatially defined image as shown in FIG. 7.

The fundamental frequency echo signals are coupled to a B mode processor 36 which produces a standard B mode tissue image. The B mode processor performs in the same manner as the contrast image processor, but operates on fundamental frequency echoes. The echo signals are amplitude (envelope) detected and scan converted to produce a spatially delineated image of tissue in the image field. The contrast and B mode images are coupled to an image processor 40 which does the image processing needed to display the images on an image display 42. This may include displaying two images at the same time, side-by-side, as shown in FIG. 7. It may also comprise overlaying parameter colors over the contrast images so that perfusion parameters are shown in relation to the tissue structure in which the contrast agent which led to the calculation of the parameters is located.

In accordance with the principles of the present invention the harmonic echo signals are coupled to a TIC processor 50. The TIC processor processes echo signals from a contrast agent received over time from regions of interest (ROIs) to produce time-intensity curves such as those shown in FIG. 2a. As mentioned above, this processing involves acquiring echo signals over time from contrast agent washing into and out of the vessels and capillaries of regions of interest in tissue (e.g., liver parenchyma) and fitting this echo data to a smooth curve. Since a contrast agent can be applied in a bolus injection, and can also be disrupted by relatively intense ultrasound which breaks or diffuses the microbubbles which are then allowed to reperfuse the ROI, temporal characteristics of the arrival and departure of the contrast agent can be measured and used for supporting diagnosis. A common measure is the time-intensity curve of the arrival and departure of the contrast agent as described in U.S. Pat. No. 5,833,613 (Averkiou et al.) A time-intensity curve can be calculated for each point in an image of perfused tissue and one or more parameters of each curve for each image point can be displayed in grayscale shades or color-coding to form a parametric image of perfusion as described in U.S. Pat. No. 6,692,438 (Skyba et al.) These parameters include the peak, time to peak, and the mean slope of the rise of the curves, each indicating a different characteristic of the tissue perfusion.

A time-intensity curve is generally computed by measuring the intensity of signals returned from the contrast agent as it flows into and out of blood vessels and the microvasculature of the tissue. These measurements of the rise and fall of the amount of contrast agent are then fitted to a curve such as that defined by the Gamma-variate curve model $$A*(x-t_0)*\exp(-\beta*(x-t_0))+C,$$

where A is the curve peak, $t_0$ is the time of initiation of the increase of contrast agent, $\mathbf{x}$ is the slope of the rise of the curve, and x is the instantaneous measurement of the amount of the contrast agent at the ROI. These time and intensity representations provide an indication to a trained clinician of the manner in which the tissue is perfused.

In an implementation of the present invention a time-intensity curve is formed from the contrast wash-in and wash-out at each ROI of a continuous field of ROIs over the liver parenchyma. This provides the ability to calculate a time-intensity curve parameter at each point in an image of the liver. As contrast agent begins to flow into the liver, points in a contrast image of the liver begin to brighten as contrast builds up to a maximum intensity, then dim as the contrast agent flows out of the liver. It is this increase and decrease of contrast intensity at each ROI which is represented by a time-intensity curve for the ROI. The detected brightness change will not follow a smooth curve, but will be detected as a plurality of points which generally follow an increasing and decreasing curve. It is this variability in the detected intensity which is the reason for curve-fitting, so that a smooth curve can be used for parameters rather than data with great variability.

Figure 5:
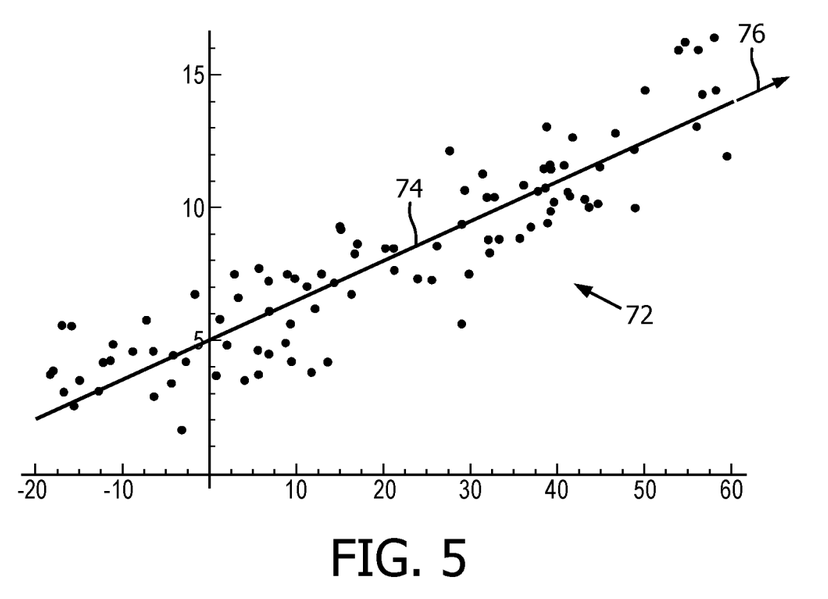
FIG. 5 illustrates the production of a curve from acquired data values by linear regression.

A time-intensity curve can be formed in two ways. One is to accumulate the signal data for each ROI over the full wash-in, wash-out cycle, then fit a curve to the complete set of data at the end of the cycle. This can be done from real time data acquisition where the source of echo signals is an ultrasound transducer, or using contrast images stored in Cineloop® memory 24 from an earlier acquisition, in which case the source of echo signals is an image memory. The other way is to form the time-intensity curve in real time as the echo signal data is received. This can be done by fitting or estimating partial curves to the most recently received signal data, such as the most recent 10-15 echoes. Another way is to smooth the echo data as by filtering it with a dual moving average filter. Yet another way is to estimate a linear regression coefficient for the most recently received data. This is illustrated in FIG. 5, where the dots indicated at 72 represent received data points. It is seen that the dots do not define a continuous curve, but generally follow a mean curve such as line 74 in the drawing, which is calculated from a linear regression analysis of the data points 72. A standard form of linear regression model which can be used operates on a matrix of data (echo signal) values is $$y=X\beta+\varepsilon$$

when expressed in vector form. Yet another way to form the time-intensity curve as data is received is to extrapolate further extension of a curve to predict a shape, then validate or alter the extrapolation with subsequently received filtered data. In these ways, the time-intensity curves for the ROIs are computed as the contrast echo signal data is received over the wash-in, wash-out cycle, and parametric images formed for one or more points in time in the cycle or as a constantly changing image with time as data is received.

Time-intensity curves formed by the TIC processor 50 for each point (ROI) in a contrast image of the liver are stored in time-intensity curve memory 52. The curves are then processed by a TIC change estimator 54 as described in conjunction with FIG. 2 to produce new curves of time-variable parameters. Preferred parameters are the first and second derivatives, which are calculated as explained in conjunctions with FIGS. 2 and 3. A desired variable is selected by user manipulation of a control on the user control 20 to select one or more desired derivatives, e.g., the first derivative, second derivative, or both. The numerical derivative values are applied to a color map look-up table (LUT) 56, where they are converted to corresponding color values. The colors can be those of a range of colors as is done for colorflow imaging and would generally be done for a parametric image of a parameter of the original time-intensity curves, or can be just two colors when binary parametric images of polarity are desired as described above. The desired color map is selected by the user by means of the user control. The resulting map or maps of color parameters are then overlaid over an anatomically corresponding contrast image from the contrast image processor, which produces the final parametric image. The image is coupled to an image processor 40, which displays the parametric image on an image display 42, either alone or side-by-side with a contrast image or a B mode image from the B mode processor.

Figure 6:
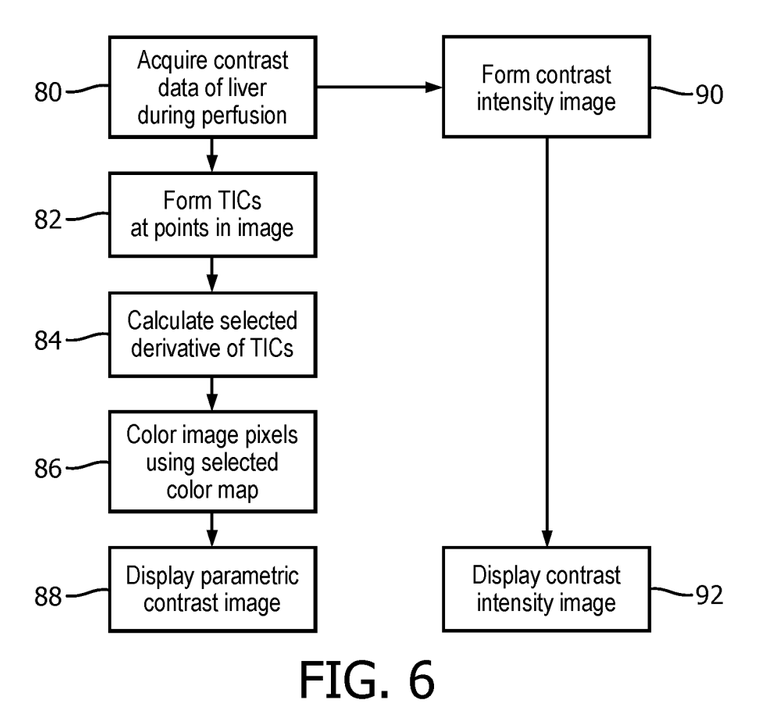
FIG. 6 illustrates a method for producing a contrast intensity image and a parametric contrast image in accordance with the present invention.

The steps of an exemplary method in accordance with the present invention is shown in FIG. 6. In step 80 contrast echo signal data is acquired from a liver as it is perfused with a contrast agent during a wash-in, wash-out cycle. This may be done in real time during live imaging, or by using previously acquired contrast images of a wash-in, wash-out cycle retrieved from storage in memory. The contrast echo signal data is used to form contrast intensity images over the cycle in step 90. In step 82 time-intensity curves of the increase and decrease of contrast intensity at points (pixels)

in the liver image are calculated, generally by curve-fitting to a curve model as described above. In step 84, one or more time-dependent parameters (e.g., derivative values or curves) are calculated from the time-intensity curves and in step 86 the time-dependent parameters are converted to colors and mapped to their locations in an anatomical image overlay. The parametric color overlay is combined with the anatomically corresponding contrast image and displayed in step 88. If desired, the contrast intensity image may be displayed concurrently in step 92 with the parametric image such as in a side-by-side display.

Ultrasound images produced following steps 92 and 88 and taken from a reduction to practice of the present invention are shown side-by-side in FIG. 7. On the left is a contrast intensity image 92' of a liver, FIG. 7a, which was acquired at the 27.4 second mark of a wash-in, wash-out cycle of contrast agent. It can be seen that there are some regions of the image which are brighter than others due to greater concentrations of contrast agent, on the left side of the image and in the lower center of the image. These may be suspicious areas where a lesion might be present. To the right of the contrast intensity image 92' in FIG. 7b is a time-dependent parametric image 88' of the same liver acquired at the same time in the procedure. The parametric image 88' is an image of the polarity of the first derivative parameter of the time-intensity curves (FIG. 2b), also produced at the same 27.4 second mark of the procedure. This image is seen to highlight the same area of the liver on the left side and at the bottom center of the image. It is also seen to highlight a roughly triangular area 68 above the center of the image, which is virtually invisible in the contrast image 92'. It is seen that the time-dependent parametric image, and in particular an image of the polarity of the parameter, highlights suspicious regions of the anatomy which are virtually indistinguishable in the contrast image. The image 88' is even more dramatic in the original, where normal tissue in the image is colored red and the suspicious areas such as 68 are colored green.

Other variations and modifications will readily occur to those skilled in the art. For instance, to even better highlight areas of possible lesions, the time-intensity curves may be normalized to normal tissue data. When a clinician is viewing a parametric or contrast image where a region of normal tissue is definitively shown, the clinician can position a cursor over the normal tissue of the image and click to select that ROI. This ROI Select command controls the beamformer 30 in FIG. 4 to delineate the contrast data from the selected ROI as produced by normal tissue. The resulting time-intensity curve from the ROI is then taken as that of normal tissue, and is subtracted from the other time-intensity curves stored in the TIC memory 52. The subtraction will substantially cancel time-intensity curves returned from normal tissue, whereas the subtraction will have only a small or negligible effect on time-intensity curves produced from lesionous regions. The resulting parametric image will have little or no content (e.g., will be black) where normal tissue is present, and will have at least a small and generally significant intensity where tumorous tissue is present.

It should be noted that the ultrasound system which acquires contrast echo signal data from perfusion in the liver and processed it to form a parametric image of a time-dependent parameter as shown in FIG. 4 and in the method of FIG. 6, and in particular the component structure of the ultrasound system of FIG. 4, may be implemented in hardware, software or a combination thereof. The various embodiments and/or components of an ultrasound system, for example, the modules, or components and controllers therein, also may be implemented as part of one or more computers or microprocessors. The computer or processor may include a computing device, an input device, a display unit and an interface, for example, for accessing the Internet. The computer or processor may include a microprocessor. The microprocessor may be connected to a communication bus, for example, to access a PACS system which stores previously acquired contrast images. The computer or processor may also include a memory. The memory devices such as the A-line memory 24 may include Random Access Memory (RAM) and Read Only Memory (ROM). The computer or processor further may include a storage device, which may be a hard disk drive or a removable storage drive such as a floppy disk drive, optical disk drive, solid-state thumb drive, and the like. The storage device may also be other similar means for loading computer programs or other instructions into the computer or processor.

As used herein, the term "computer" or "module" or "processor" may include any processor-based or microprocessor-based system including systems using microcontrollers, reduced instruction set computers (RISC), ASICs, logic circuits, and any other circuit or processor capable of executing the functions described herein. The above examples are exemplary only, and are thus not intended to limit in any way the definition and/or meaning of these terms.

The computer or processor executes a set of instructions that are stored in one or more storage elements, in order to process input data. The storage elements may also store data or other information as desired or needed. The storage element may be in the form of an information source or a physical memory element within a processing machine.

The set of instructions of an ultrasound system including the acquisition of contrast data and the calculation of time-intensity curves and parameters described above may include various commands that instruct a computer or processor as a processing machine to perform specific operations such as the methods and processes of the various embodiments of the invention. The set of instructions may be in the form of a software program. The software may be in various forms such as system software or application software and which may be embodied as a tangible and non-transitory computer readable medium. Further, the software may be in the form of a collection of separate programs or modules, a program module within a larger program or a portion of a program module. For example, the curve-fitting equations calculated by the time-intensity data processor of FIG. 4, the derivatives calculated by the time-intensity change estimator, and the color values calculated by the color map look-up table may be executed by software modules calculating the equations. The software also may include modular programming in the form of object-oriented programming. The processing of input data by the processing machine may be in response to operator commands, or in response to results of previous processing, or in response to a request made by another processing machine. In the imaging and time-intensity curve calculation portions of FIG. 4, for instance, software instructions are conventionally employed to calculate the equations given above.

Furthermore, the limitations of the following claims are not written in means-plus-function format and are not intended to be interpreted based on 35 U.S.C. 112, sixth paragraph, unless and until such claim limitations expressly use the phrase "means for" followed by a statement of function devoid of further structure.

What is claimed is:

1. An ultrasonic imaging system for analyzing characteristics of liver perfusion comprising:
   a source of ultrasound echo signals acquired in the presence of contrast agent flow;
   a nonlinear signal separator, coupled to receive the ultrasound echo signals acquired in the presence of the contrast agent flow, and configured to produce echo signal data from the contrast agent flow;
   a time-intensity curve processor, responsive to the echo signal data from the contrast agent flow, which is configured to produce a time-intensity curve of the contrast agent flow in a region of interest;
   a time-intensity curve change estimator, responsive to the time-intensity curve, which is configured to produce a plurality of time-dependent parameters of the time-intensity curve, wherein the plurality of time-dependent parameters comprises a derivative with respect to time of the time-intensity curve;
   a color map processor, responsive to the plurality of time-dependent parameters, which is configured to produce a binary color map; and
   an image processor, which is configured to, based on the binary color map, produce a parametric image which is a function of the polarity of the derivative with respect to time of the time-intensity curve.

2. The ultrasonic imaging system of claim 1, wherein the derivative with respect to time comprises the first derivative with respect to time of the time-intensity curve, and wherein the time-intensity curve change estimator is further configured to calculate the second derivative with respect to time of the time-intensity curve.

3. The ultrasonic imaging system of claim 1, wherein the source of ultrasound echo signals further comprises an ultrasound transducer or an image memory.

4. The ultrasonic imaging system of claim 1, wherein the nonlinear signal separator is further configured to produce harmonic echo signal data from the contrast agent flow by filtering or pulse inversion.

5. The ultrasonic imaging system of claim 1, wherein the time-intensity curve processor is further configured to produce a plurality of time-intensity curves for a plurality of pixel locations in a liver image.

6. The ultrasonic imaging system of claim 1, wherein:
   the color map processor is further configured to produce an additional binary color map; and
   the image processor is further configured to, based on the additional binary color map, produce an additional parametric image.

7. The ultrasonic imaging system of claim 1, wherein the color map processor further comprises a color look-up table.

8. The ultrasonic imaging system of claim 6, wherein the additional parametric image is a function of the polarity of an additional derivative with respect to time of the time-intensity curve.

9. A method for ultrasonically displaying liver perfusion parameters comprising:
   acquiring echo data from a contrast agent during a wash-in, wash-out cycle;
   forming time-intensity curves of the echo data for points in a liver image;
   calculating time-dependent parameters of data values of the time-intensity curves, wherein the time-dependent parameters comprise a derivative with respect to time of the data values of the time-intensity curves;
   coloring image pixels of an anatomical parametric image in relation to the polarity of the derivative with respect to time of the data values and a binary color map; and
   displaying the anatomical parametric image of the derivative with respect to time.

10. The method of claim 9, wherein calculating the derivative with respect to time of the data values of the time-intensity curves comprises calculating at least one of the first derivative or the second derivative with respect to time of the data values of the time-intensity curves.

11. The method of claim 9, wherein calculating the derivative with respect to time of the data values of the time-intensity curves further comprises calculating at least one of the rate of change of the time-intensity curves or the acceleration of the change of the time-intensity curves.

12. The method of claim 9, further comprising:
   coloring image pixels of an additional anatomical parametric image in relation to an additional binary color map.

13. The method of claim 12, comprising coloring image pixels of the additional anatomical parametric image further in relation to the polarity of an additional derivative with respect to time of the data values of the time-intensity curves.

14. The method of claim 9, further comprising:
   forming an anatomical contrast image using the acquired echo data from the contrast agent; and
   displaying the anatomical contrast image with the display of the anatomical parametric image.

15. The method of claim 14, wherein coloring image pixels of the anatomical parametric image further comprises overlaying the anatomical contrast image with the anatomical parametric image.

* * * * *